US00PP18279P3

(12) United States Plant Patent
Stemkens

(10) Patent No.: US PP18,279 P3
(45) Date of Patent: Dec. 4, 2007

(54) *GAURA* PLANT NAMED 'GAUDROS'

(50) Latin Name: *Gaura lindheimeri*
Varietal Denomination: Gaudros

(75) Inventor: Henricus G. W. Stemkens, EB Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 24 days.

(21) Appl. No.: 11/299,619

(22) Filed: Dec. 12, 2005

(65) Prior Publication Data

US 2007/0136909 P1 Jun. 14, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—Bruce Vrana

(57) ABSTRACT

A new and distinct variety of *Gaura* plant, substantially as herein illustrated and described, characterized particularly as to novelty by a well-branched, compact habit, continuous flowering, pink flowers, green foliage and early to flower.

1 Drawing Sheet

Latin name of the genus and species of the plant claimed: *Gaura lindheimeri.*
Varietal denomination: 'Gaudros'.

BACKGROUND OF THE NEW PLANT

The present invention comprises a new and distinct *Gaura* plant, botanically known as *Gaura lindheimeri,* and hereinafter referred to by the cultivar name 'Gaudros.'

The new cultivar was developed by the inventor in a controlled breeding program during 2000, at Enkhuizen, The Netherlands. The new *Gaura* cultivar is characterized by a well-branched, compact habit, continuous flowering, green foliage and early to flower.

The female (seed) parent of 'Gaudros' was 'B0012-1,' an unpatented *Gaura lindheimeri* that is not known by any synonyms. The male (pollen) parent of 'Gaudros' was 'C0013-1,' also an unpatented *Gaura lindheimeri* that is not known by any synonyms. 'Gaudros' was selected in May 2001 as a single flowering plant from within the F2 progeny of the above stated cross and was initially designated 'D0010-1.'

Asexual reproduction of the new cultivar at Enkhuizen, The Netherlands and Sarrians, France was carried out by the use of terminal stem cuttings, and has demonstrated that the new variety is stable and reproduces true to type in successive generations of asexual reproduction.

SUMMARY OF THE INVENTION

It was found that the cultivar of the present invention:

a) Exhibits pink flowers;

b) Forms green foliage; and c) Exhibits an upright and very well branched growth habit

DESCRIPTION OF THE DRAWING

This new *Gaura* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Gaura.* The data which defines these characteristics were collected from asexual reproductions carried out in Enkhuizen, Netherlands. The plant history was taken on 16 week old plants blossomed under natural light in a greenhouse and grown in a 13 cm container.

Color readings were taken in the greenhouse under ambient light. Color references are primarily to The R.H.S. Colour Chart of The Royal Horticultural Society of London.

TABLE 1

DIFFERENCES BETWEEN THE NEW CULTIVAR 'GAUDROS', ITS PARENTS AND A SIMILAR CULTIVAR

| | 'Gaudros' | 'B0012-1' | 'C0013-1' | 'Siskyou Pink' |
|---|---|---|---|---|
| Flower color | Pink | Rose | White | Light Pink |
| Height | 50 cm | 80 cm | 60 cm | 60 cm |
| Branching | Very good | Good | Poor | Poor |

'Siskyou pink' is not patented.

The plant:

*Classification.*—Botanical: *Gaura lindheimeri.*

*Cultivar name.*—'Gaudros'.

*Parentage.*—Female parent: A seedling named 'B0012-1' is one of our seedlings from our B-generation of plants bred in 1999. Pollen parent: A seedling named 'C0013-1' is one of our seedlings from our C-generation of plants bred in 2000.

*Growth habit.*—Upright.

*Plant height.*—50–70 cm.

*Spreading area of plant.*—20–30 cm.

*Strength.*—Very resistant to hot and cold weather.

*Branching habit.*—Freely branching and lateral branching at every node.
*Number of lateral branches.*—15–30.
*Blooming period.*—From May until November.
*Propagation.*—Vegetative stem cuttings.
*Sexuality.*—Hermaphrodite.
*Time to initiate roots.*—Approximately 12 days at temperatures of 22 degrees centigrade is needed to produce rooted cuttings.
*Root system.*—Fibrous, branching, the color is N157C.

The stem:
*Diameter.*—2–4 mm.
*Length.*—50–70 cm.
*Shape.*—Round.
*Anthocyan pigmentation.*—Present, color 185A.
*Color of the stem.*—138C.
*Length of internode.*—20–40 mm.
*Pubescence.*—Slightly pubescent.

The foliage:
*Phyllotaxis.*—Alternate.
*Shape of blade.*—Lanceolate to oblanceolate.
*Attachment.*—Sessile.
*Texture.*—Upper side: Slightly pubescent. Lower side: Slightly pubescent.
*Venation.*—Pinnate.
*Leaf margin.*—Entire to very slightly dentate.
*Leaf base.*—Attenuate.
*Leaf apex.*—Acute.
*Length.*—20–45 mm.
*Width.*—10–23 mm.
*Depth of incision.*—Less than 1 mm.
*Color.*—Upper side: 146A. Lower side: 146B.
*Color of venation.*—Upper side: 143B. Lower side: 143C.

The bud:
*Peduncle length.*—12–18 cm.
*Peduncle diameter.*—2–3 mm.
*Peduncle strength.*—Moderately strong.
*Peduncle texture.*—Smooth, glabrous.
*Peduncle angle.*—Upright.
*Peduncle color.*—141C.
*Pedicel length.*—3–6 mm.
*Pedicel diameter.*—1 mm.
*Pedicel color.*—181B.
*Pedicel surface.*—Slightly hairy.
*Stipule length.*—1–3 mm.
*Stipule width.*—1–2 mm.
*Stipule shape.*—Lanceolate.
*Stipule color.*—Upper side: 146C. Lower side: 146C.
*Bud size.*—Diameter: 2 mm. Length: 6–8 mm.
*Bud shape.*—Tubular.
*Bud colour.*—182D.
*Bud surface.*—Pubescent.
*Sepals.*—Color (Upper side): 182D. Color (Lower side): 182D. Form: Upright. Surface (Upper side): Pubescent. Surface (Lower side): Pubescent. Number: 4, fused at tip. Length: 7–11 mm. Width: 1.5–2.5 mm. Shape: Tubular. Apex: Acute. Base: Subcordate. Margin: Entire.

The flower:
*Type of inflorescence.*—Spicate raceme.
*Flower shape.*—Single, cruciform.
*Flower color.*—Upper side: 68B. Lower side: 68A.
*Flower size.*—Height: 14–16 mm. Width: 18–20 mm.
*Petals, number.*—4, non-overlapping.
*Petal shape.*—Oblanceolate.
*Petal margin.*—Entire.
*Petal apex.*—Acute to obtuse.
*Petal base.*—Attenuate.
*Petal length.*—7–9 mm.
*Petal width.*—7–9 mm.
*Petal texture.*—Upper side: Smooth. Lower side: Smooth.
*No. of flowers per inflorescence.*—40–60.
*Length of inflorescence* (*at end of flowering cycle*).—25–60 cm.
*Inflorescence diameter.*—5–6 cm.
*Fragrance.*—No fragrance.
*Bloom time of one inflorescence.*—New florets continue to open in one inflorescence over a period of 25 days.
*Lastingness of one flower on the plant.*—3–4 days.
*Lastingness of one flower off the plant.*—Less than 12 hours.
*Number of flowers open at one time in one inflorescence.*—1–2.

The reproductive organs:
*Androecium.*—Stamens quantity: 8. Stamen length: 12 mm. Stamen colour: N155A. Anther shape: Elongated. Anther length: 0.8 mm. Anther width: 0.2 mm. Anther color: 9D. Pollen amount: Plentiful pollen. Pollen color: 9D.
*Gynoecium.*—Pistils quantity: 1. Pistil length: 12 mm. Stigma color: 4D. Stigma shape: Lobed. Number of lobes: 4. Style color: N155A. Ovary color: 141D. Ovary position: Inferior. Ovary shape: Elongated. Ovary dimensions: 0.2 mm in width and 0.5 mm in length.

Seeds:
*One seed is formed per flower.*—Seed size — Length: 3 mm. Width: 1 mm.
*1000* seeds weight.—4.5 grams.
*Seed color.*—185B.
*Seed texture.*—Smooth.

Disease/pest resistance: Plants of the new *Gaura* have not been noted to be resistant to pathogens or pests common to *Gaura*.

Temperature tolerance: Plants of the new *Gaura* have been observed to tolerate temperatures ranging from −10 degrees C. to 35 degrees C.

Hardiness: zone 'Gaudros' is hardy in zones eight (8) and above.

What is claimed is:

1. A new and distinct cultivar of *Gaura* plant named 'Gaudros,' as substantially illustrated and described herein.

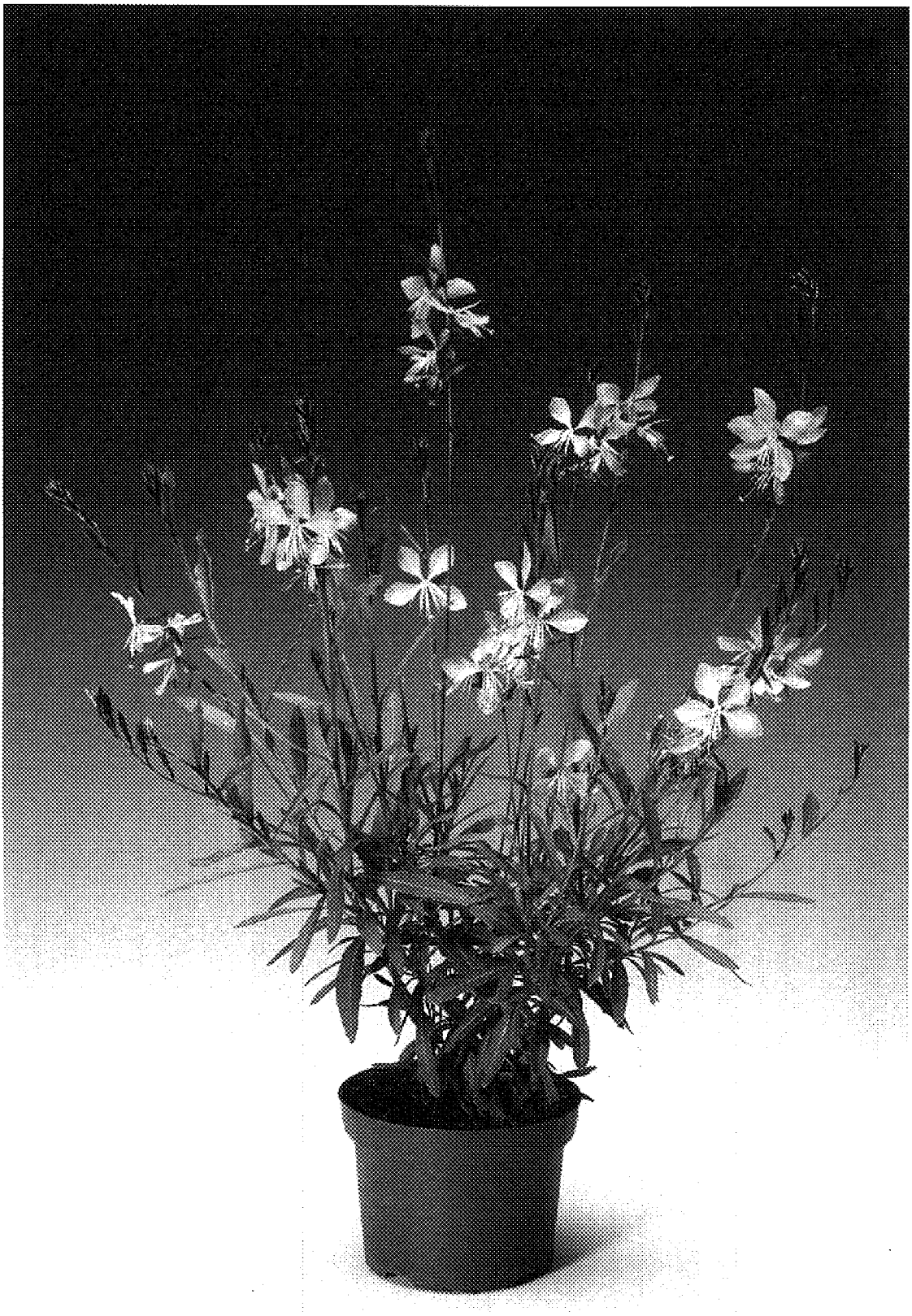

* * * * *